United States Patent [19]

Schaefer

[11] Patent Number: 4,581,389

[45] Date of Patent: Apr. 8, 1986

[54] METHOD FOR PHOTOPOLYMERIZATION OF VINYL COMPOUNDS AND PHOTOPOLYMERIZABLE MATERIALS USED IN SAID PROCESS USING 1-ARYL-2,5 DIALKYPYRROLE AS REDUCING AGENT

[75] Inventor: Roland Schaefer, Friedrichsdorf, Fed. Rep. of Germany

[73] Assignee: Kulzer & Co. GmbH, Wehrheim, Fed. Rep. of Germany

[21] Appl. No.: 568,376

[22] Filed: Jan. 5, 1984

[30] Foreign Application Priority Data

Jan. 14, 1983 [DE] Fed. Rep. of Germany ....... 3301010

[51] Int. Cl.[4] .................. C08F 2/50; C08L 63/10
[52] U.S. Cl. ................................... 522/9; 522/14; 522/26; 522/63; 522/10; 522/50; 522/83; 522/910; 522/103
[58] Field of Search .............. 204/159.18, 159.24, 204/159.23

[56] References Cited

U.S. PATENT DOCUMENTS

| | | | |
|---|---|---|---|
| 3,066,112 | 11/1962 | Bowen | 523/116 |
| 4,008,085 | 2/1977 | Lemahieu | 430/336 |
| 4,025,347 | 5/1977 | Beretta et al. | 430/588 |
| 4,071,424 | 1/1978 | Dart et al. | 204/159.15 |
| 4,197,120 | 4/1980 | Wright | 430/32 |
| 4,243,578 | 1/1981 | O'Sullivan et al. | 523/116 |
| 4,267,133 | 5/1981 | Kohmura et al. | 264/18 |
| 4,307,182 | 12/1981 | Dalzell | 430/914 |
| 4,382,102 | 5/1983 | Noomen | 427/54.1 |

FOREIGN PATENT DOCUMENTS

| | | |
|---|---|---|
| 049922 | 4/1982 | European Pat. Off. . |
| 569974 | 6/1945 | United Kingdom . |
| 1408265 | 10/1975 | United Kingdom . |
| 1428672 | 3/1976 | United Kingdom . |
| 2018666 | 10/1979 | United Kingdom . |

OTHER PUBLICATIONS

Roffey "Photopolym . . ." 1982, Wiley & Sons, pp. 68, 69, 70, 71, 73, 85, 88, 97, 98.

*Primary Examiner*—John C. Bleutge
*Assistant Examiner*—A. H. Koeckert
*Attorney, Agent, or Firm*—Frishauf, Holtz, Goodman & Woodward

[57] ABSTRACT

A method for the production of a polymer composition comprising photopolymerizing at least one vinyl compound in the presence of at least one photoinitiator, said photoinitiator comprising at least one photosensitizer and at least one reducing agent selected from compounds of formula I and II. Polymerizable materials containing said photoinitiators and said at least one vinyl compound are also disclosed. The polymerizable materials are particularly suited for use as dental materials.

21 Claims, No Drawings

METHOD FOR PHOTOPOLYMERIZATION OF VINYL COMPOUNDS AND PHOTOPOLYMERIZABLE MATERIALS USED IN SAID PROCESS USING 1-ARYL-2,5 DIALKYPYRROLE AS REDUCING AGENT

BACKGROUND OF THE INVENTION

The present invention provides a process for the photopolymerization of vinyl compounds in the presence of a photoinitiator.

Photopolymerization has many useful technical applications as, for example, for the curing of lacquers and coatings, in the manufacture of printing plates and in letter press printing.

Photopolymerization is also useful in the dental field. Photopolymerizable materials are used in the preparation of dental fillings and sealings, of crowns and bridges and artificial teeth and dentures (see, for example, British Pat. No. 569,974, DE-OS No. 31 36 484.5 corresponding to U.S. Ser. No. 413,804 filed Sept. 1, 1982, GB No. 1 428 672, U.S. Pat. No. 4,243,578, U.S. Pat. No. 4,267,133 and GB No. 2 018 666A).

British Pat. No. 1 408 265 described photopolymerizable materials which contain as a photoinitiator a mixture of:
(a) at least one photosensitizer of the formula

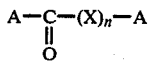

where X is CO, $C(R^1)(R^2)$ or $C(R^3)(OR^4)$, $R^1, R^2, R^3, R^4$, which may be the same or different, are hydrogen or hydrocarbyl groups; n is 0 or 1; and the groups A, which may be the same or different, are hydrocarbyl or substituted hydrocarbyl groups, and in which the groups A may be further linked together by a direct link or by a divalent hydrocarbyl group, or in which the groups A together may form a fused aromatic ring system, the groups A being aromatic or substituted aromatic when n is 1 and X is $C(R^1)(R^2)$ and when n is 0, and (b) at least one reducing agent capable of reducing the photosensitizer when the photosensitizer is in an excited state and having the structure

where M is an element of Group V B of the Periodic Table and the units R, which may be the same or different, are hydrogen atoms, hydrocarbyl groups, substituted hydrocarbyl groups or groups in which two units R together with the element M for a cyclic ring system, no more than two of the units R being hydrogen atoms or substituted hydrocarbyl groups and where element M is attched directly to an aromatic group R, at least one of the other units R has a

group attached to M.

The resulting mixtures can be cured by exposure to visible or ultraviolet light. Examples of the photosensitizers include biacetyl, benzil, p,p'-dialkoxybenzil, benzoin and camphorquinone. Reducing agents include propylamine, dimethylaminoethyl methacrylate, N,N'-dimethylaniline and piperidine.

German patent application No. P 31 36 484.5 discloses a method for the photopolymerization of vinyl compounds in the presence of ketones as photosensitizers and cyclic or heterocyclic compounds, particularly 5-substituted barbituric acids, which are used as reducing agents.

It is an object of the present invention to provide a method of photopolymerizing vinyl compounds which results in rapid curing of the vinyl compounds. The resulting polymers produced according to the present invention have excellent color fastness.

SUMMARY OF THE INVENTION

The present invention provides a process for the photopolymerization of vinyl compounds in the presence of a photoinitiator comprising:
(a) at least one photosensitizer of the formula

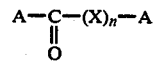

wherein
X is selected from CO, $C(R^1)(R^2)$ or $C(R^3)(OR^4)$, $R^1$, $R^2$, $R^3$, $R^4$ are each selected from a hydrogen atom or a hydrocarbon radical;
n is 0 or 1;
A are hydrocarbon radicals which may be substituted and which may be bonded together, with the proviso that when A is 1 and
X is $C(R^1)(R^2)$, and when n is 0, then A is an aromatic radical; and
(b) at least one reducing agent selected from compounds of formula I and II:

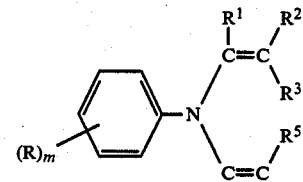

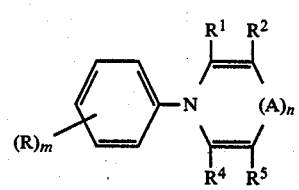

wherein
R is selected from the group consisting of a halogen atom, an alkyl radical, an aryl radical, an alkoxy radical and an aryloxy radical, which radicals may be substituted;
$R^1$ and $R^4$ are each selected from the group consisting of an alyl, alkenyl and aryl radical, wherein said radicals may be the same or different;
$R^2$, $R^3$, $R^5$ and $R^6$ are each selected from the group consisting of a hydrogen atom, an alkyl radical, an alkenyl radical and an aryl radical, wherein said radicals may be the same or different;

m is an integer of 0–5;

n is 0 or 1;

A is selected from the group consisting of $C(R^7)(R^8)$, CO and CS, wherein $R^7, R^8$ are each selected from the group consisting of a hydrogen atom, an alkyl radical and an aryl radical.

Preferably R is selected from the group consisting of a halogen atom, an alkyl radical with 1 to 5 carbon atoms, a phenyl radical, which may be substituted, an alkoxy radical with 1 to 5 carbon atoms and a phenoxy radical, which may be substituted.

Most preferably R is a phenyl or a substituted phenyl radical.

Preferably $R^1$ and $R^4$ are each selected from the group consisting of an alkyl radical with 1 to 5 carbon atoms, an alkenyl radical with 2 to 5 carbon atoms and a phenyl radical.

Most preferably $R^1$ and $R^4$ are alkyl radicals with 1 to 3 carbon atoms.

Preferably $R^2$, $R^3$, $R^5$ and $R^6$ are each selected from the group consisting of hydrogen atom, an alkyl radical with 1 to 5 carbon atoms, an alkenyl radical with 2 to 5 carbon atoms and a phenyl radical.

Most preferably $R^2$, $R^3$, $R^5$, and $R^6$ are hydrogen atoms.

Preferably $R^7$ and $R^8$ are each selected from the group consisting of a hydrogen atom, an alkyl radical with 1 to 5 carbon atoms and a phenyl radical.

It is particularly desirable to use 1-aryl-2,5-dialkyl-pyrroles as the reducing agent such as 1-(3,4-dimethylphenyl)-2,5-dimethylpyrrole, 1-(4-ethoxycarbonylphenyl)-2,5-dimethylpyrrole, 1-(2,4,6-trimethylphenyl)-2,5-dimethylpyrrole and p,p'-di(2,5-dimethylpyrrolyl)-diphenylsulfone. Benzoin alkyl ethers and alpha-diketones are the preferred photosensitizers. The preferred benzoin alkyl ether is benzoin methyl ether. The preferred alpha-diketones are selected from benzil and camphorquinone. It is also desirable to use, in addition to benzil or camphorquinone, a 2,2-dialkoxy-1,2-diphenylethanone such as 2,2-dimethoxy-1,2-diphenylethanone. A particularly suitable photosensitizer is a mixture of camphorquinone and 2,2-dimethoxy-1,2-diphenylethanone. Applicant has discovered that photopolymerization in the presence of carbonyl compounds is accelerated to a greater degree of N-aryl-amines having no CH groups in the alpha-position than by the N-aryl-amine compounds disclosed in British Pat. No. 1 408 265.

The present process is applicable whenever monomer vinyl compounds or compositions containing these compounds can be polymerized by exposure to ultraviolet or visible light.

The vinyl compounds which may be polymerized in accordance with the present invention include all commonly used ethylene-like unsaturated compounds, especially vinyl chloride and esters of acrylic and methacrylic acids with monohydric and polyhydric alcohols. Also included are the so-called urethane acrylates and methacrylates as disclosed in U.S. Pat. No. 3,825,518 incorporated herein by reference and bis-GMA as shown in U.S. Pat. No. 3,066,112 incorporated herein by reference, which is the reaction product of bisphenol A and glycidylmethacrylate, bis-[4-(2-hydroxy-3-methacryloyloxypropoxy)-phenyl]-dimethylmethan.

In practice, the photosensitizer is added to the vinyl compounds or to the compositions containing those compounds, in an amount of between 0.01 to 10% by weight of the vinyl compounds. The preferred amount is between 0.1 and 5% by weight. The reducing agent can be provided in an amount within the same range as the photosensitizer.

The application of the process of the present invention has been found particularly useful in the field of dentistry for the preparation of dental fillings and sealings, as well as crowns, bridges and artificial teeth and dentures. Polymerization of esters of acrylic or methacrylic acid by exposure ro ultraviolet or visible light, and especially in the presence of materials containing inorganic fillers, is particularly suited for this purpose.

The following examples are submitted for the purpose of illustrating the invention and are not intended to limit the invention covered by the claims appended hereto. Examples 1–3 show polymerization in accordance with the present invention using irradiation with ultraviolet light while Examples 4–8 show polymerization with visible light of esters of methacrylic acid and photopolymerizable materials containing inorganic fillers.

Comparative Examples 9–12 show the polymerization of photopolymerizable materials using, as a reducing agent, N-aryl-N compounds with CH groups located in the position adjacent to the nitrogen atom.

The thickness of the layer of the solid polymer body thus obtained serves as means of evaluating and comparing the photoinitiator activity.

EXAMPLES 1–3

Polymerization by irradiation with ultraviolet light

A mixture of 7 grams bis-GMA, 3 grams triethyleneglycoldimethacrylate, 30 grams lithium aluminum silicate (85 weight % of which comprise particles smaller than 15 micrometers), 1 gram aluminum oxide having a particle size less than 5 micrometers, and X of a photoinitiator (see Table 1)

are placed in a tube (inner diameter 6 mm, height 10 mm) of Delrin, a trademarked product made of a polyacetal plastic, covered with mylar foil; and irradiated for 20 seconds by a DURALUX-brand ultraviolet polymerization apparatus manufactured by Kulzer & Company GmbH, Model DURALUX UV 20A, whose lens or output window is placed on the mylar foil.

The portion of the mixture remaining unpolymerized is removed, and the thickness of the layer of the polymerized portion is measured.

The type and quantity of the photoinitiator and the thickness of the polymerized layer are shown in Table I.

TABLE 1

| Example | Photoinitiator | Weight % | Layer Thickness (mm) |
|---|---|---|---|
| 1 | benzoinmethylether | 0.1 | 2.2 |
|  | + | 0.1 |  |
|  | 1-(3,4-dimethylphenyl)-2,5-dimethylpyrrole |  |  |
| 2 | benzil | 0.1 | 1.7 |

TABLE 1-continued

| Example | Photoinitiator | Weight % | Layer Thickness (mm) |
|---------|----------------|----------|----------------------|
|  | + | 0.1 |  |
|  | 1-(3,4-dimethylphenyl)-2,5-dimethylpyrrole |  |  |
| 3 | Camphorquinone | 0.1 | 2.5 |
|  | + | 0.3 |  |
|  | 2,2-dimethoxy-1,2-diphenylethanone | 0.1 |  |
|  | + |  |  |
|  | 1-(3,4-dimethylphenyl)-2,5-dimethylpyrrole |  |  |

EXAMPLES 4-8

Polymerization of irradiation with visible light

A mixture of
7 grams bis-GMA,
3 grams triethyleneglycoldimethacrylate,
30 grams lithium aluminum silicate (85 weight % of which comprise particles smaller than 15 micrometers),
1 gram aluminum oxide having a particle size less than 5 micrometers, and
X photoinitiator (see Table 2)
are placed in a tube (inner diameter 6 mm, height 10 mm) of Delrin, a trademarked product made of a polyacetal plastic, covered with mylar foil, and irradiated for 20 seconds with a translux brand tungsten halogen lamp manufactured by Kulzer & Company GmbH, whose lens or output window is placed on the mylar foil.

The portion of the mixture remaining unpolymerized is removed and the thickness of the layer of the polymerized portion is measured.

The type and quantity of the photoinitiator and the layer thickness are shown in Table 2.

TABLE 2

| Example | Photoinitiator | Weight % | Layer Thickness (mm) |
|---------|----------------|----------|----------------------|
| 4 | camphorquinone | 0.1 | 7.5 |
|  | + | 0.1 |  |
|  | 1-(3,4-dimethylphenyl)-2,5-dimethylpyrrole |  |  |
| 5 | camphorquinone | 0.1 | 8.2 |
|  | + | 0.3 |  |
|  | 2,2-dimethoxy-1,2-diphenylethanone | 0.1 |  |
|  | + |  |  |
|  | 1-(3,4-dimethylphenyl)-2,5-dimethylpyrrole |  |  |
| 6 | camphorquinone | 0.1 | 7.1 |
|  | + | 0.3 |  |
|  | 2,2-dimethoxy-1,2-diphenylethanone | 0.1 |  |
|  | + |  |  |
|  | 1-(4-ethoxycarbonylphenyl)-2,5-dimethylpyrrole |  |  |
| 7 | camphoquinone | 0.1 | 8.2 |
|  | + | 0.3 |  |
|  | 2,2-dimethoxy-1,2-diphenylethanone | 0.1 |  |
|  | + |  |  |
|  | 1-(2,4,6-trimethylphenyl)-2,5-dimethylpyrrole |  |  |
| 8 | camphorquinone | 0.1 | 6.1 |
|  | + | 0.3 |  |
|  | 2,2-dimethoxy-1,2-diphenylethanone | 0.1 |  |
|  | + |  |  |
|  | p,p'-di-(2,5-dimethylpyrrole)-diphenylsulfone |  |  |

COMPARATIVE EXAMPLES 9-12

Polymerization by irradiation with visible light

A mixture of
7 grams bis-GMA,
3 gram triethyleneglycoldimethacrylate,
30 grams lithium aluminum silicate (85 weight % of which comprise particles smaller than 15 micrometers),
1 gram aluminum oxide having a particle size less than 5 micrometers, and
X photoinitiator (see Table 3)
are placed in a tube (inner diameter 6 mm, height 10 mm) of Delrin, a trademarked product made of a polyacetal plastic, covered with a mylar foil, and irradiated for 20 seconds with a translux brand tungsten halogen lamp manufactured by Kulzer & Company GmbH, whose lens or output window is placed on the mylar foil.

The portion of the mixture remaining unpolymerized is removed, and the layer thickness of the polymerized portion is measured.

The type and quantity of the photoinitiator and the layer thickness are shown in Table 3.

TABLE 3
(Comparison Tests)

| Example | Photoinitiator | Weight % | Layer Thickness (mm) |
|---------|----------------|----------|----------------------|
| 9 | camphorquinone | 0.1 | 4.7 |
|  | + | 0.3 |  |
|  | 2,2-dimethoxy-1,2-diphenylethanone | 0.1 |  |
|  | + |  |  |
|  | N,N—dihydroxyethyl-p-toluidine |  |  |
| 10 | camphorquinone | 0.1 | 4.8 |
|  | + | 0.3 |  |
|  | 2,2-dimethoxy-1,2-diphenylethanone | 0.1 |  |
|  | + |  |  |
|  | 1-phenylpyrrole |  |  |
| 11 | camphorquinone | 0.1 | 3.7 |
|  | + | 0.3 |  |
|  | 2,2-dimethoxy-1,2-diphenylethanone | 0.1 |  |
|  | + |  |  |
|  | 1-methylindole |  |  |
| 12 | camphorquinone | 0.1 | 4.7 |
|  | + | 0.3 |  |
|  | 2,2-dimethoxy-1,2-diphenylethanone | 0.1 |  |

TABLE 3-continued (Comparison Tests)

| Example | Photoinitiator | Weight % | Layer Thickness (mm) |
|---|---|---|---|
| | + 10-methyl-9(10H)—acridone | | |

In the formula representing the photosensitizer A and $R^1$ to $R^4$ are the same as defined in British Pat. No. 1 408 265.

I claim:

1. In a method for the production of a polymer composition comprising photopolymerizing at least one polymerizable ethylenically unsaturated compound in the presence of a photoinitiator, the improvement comprising polymerizing said at least one compound in the presence of a photoinitiator comprising:

(a) at least one photosensitizer of the formula

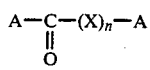

wherein X is selected from the group consisting of CO, $C(R^1)(R^2)$ and $C(R^3)(OR^4)$ and wherein $R^1$, $R^2$, $R^3$, $R^4$ are each selected from the group consisting of a hydrogen atom and a hydrocarbon radical;

n is 0 or 1;

A are hydrocarbon radicals which may be substituted and which may be bonded together, with the proviso that when n is 1 and X is $C(R^1)(R^2)$, and when n is 0, then A is an aromatic radical; and (b) at least one 1-aryl-2,5-dialkylpyrrole as a reducing agent.

2. The method of claim 1 wherein said reducing agent is selected from the group consisting of 1-(3,4-dimethylphenyl)-2,5-dimethylpyrrole, and 1-(4-ethoxycarbonylphenyl)-2,5-dimethylpyrrole.

3. The method of claim 1 wherein said photosensitizer is a benzoin alkyl ether.

4. The method of claim 1 wherein said photosensitizer is selected from the group consisting of benzil and camphorquinone.

5. The method of claim 4 wherein said photosensitizer further comprises 2,2-dialkoxy-1,2-diphenylethanone.

6. The method of claim 3 wherein said photosensitizer further comprises 2,2-dimethoxy-1,2-diphenylethanone.

7. The method of claim 4 wherein said reducing agent is selected from the group consisting of 1-(3,4-dimethylphenyl)-2,5-dimethylpyrrole, and 1-(4-ethoxycarbonylphenyl)-2,5-dimethylpyrrole.

8. The method of claim 7 wherein said photosensitizer further comprises 2,2-dialkoxy-1,2-diphenylethanone.

9. The method of claim 1 wherein said at least one photosensitizer and said at least one reducing agent are each present in an amount of between 0.01 and 10% by weight based on the weight of said at least one polymerizable ethylenically unsaturated compound.

10. The method of claim 9 wherein said at least one photosensitizer and said at least one reducing agent are each present in an amount between 0.1 and 5% by weight based on the weight of said at least one polymerizable ethylenically unsaturated compound.

11. A photopolymerizable material comprising at least one polymerizable ethylenically unsaturated compound and a photoinitiator, said photoinitiator comprising:

(a) at least one photosensitizer of the formula

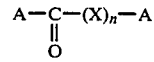

wherein X is selected from the group consisting of CO, $C(R^1)(R^2)$ and $C(R^3)(OR^4)$ and wherein $R^1$, $R^2$, $R^3$, $R^4$ are each selected from the group consisting of a hydrogen atom and a hydrocarbon radical;

n is 0 or 1;

A are hydrocarbon radicals which may be substituted and which may be bonded together, with the proviso that when n is 1 and X is $C(R^1)(R^2)$, and when n is 0, then A is an aromatic radical; and (b) at least one 1-aryl-2,5-dialkylpyrrole as a reducing agent.

12. The photopolymerizable material of claim 11 wherein said at least one photosensitizer and said at least one reducing agent are present in an amount between 0.1 and 5% by weight based on the weight of said at least one polymerizable ethylenically unsaturated compound.

13. The photopolymerizable material of claim 11 wherein said reducing agent is selected from the group consisting of 1-(3,4-dimethylphenyl)-2,5-dimethylpyrrole, and 1-(4-ethoxycarbonylphenyl)-2,5-dimethylpyrrole.

14. The photopolymerizable material of claim 11 wherein said photosensitizer is a benzoin alkyl ether.

15. The photopolymerizable material of claim 14 wherein said photosensitizer is selected from the group consisting of benzil and camphorquinone.

16. The photopolymerizable material of claim 15 wherein said photosensitizer further comprises 2,2-dialkoxy-1,2-diphenylethanone.

17. The photopolymerizable material of claim 15 wherein said photosensitizer further comprises 2,2-dimethoxy-1,2-diphenylethanone.

18. The photopolymerizable material of claim 15 wherein said reducing agent is selected from the group consisting of 1-(3,4-dimethylphenyl)-2,5-dimethylpyrrole, and 1-(4-ethoxycarbonylphenyl)-2,5-dimethylpyrrole.

19. The photopolymerizable material of claim 18 wherein said photosensitizer further comprises 2,2-dialkoxy-1,2-diphenylethanone.

20. The photopolymerizable material of claim 11 wherein said at least one photosensitizer and said at least one reducing agent are present in an amount of between 0.01 and 10% by weight based on the weight of said at least one polymerizable polymerizable ethylenically unsaturated compound.

21. The photopolymerizable material of claim 18 wherein said at least one photosensitizer and said at least one reducing agent are present in an amount between 0.1 and 5% by weight based on the weight of at least one polymerizable polymerizable ethylenically unsaturated compound.

* * * * *

UNITED STATES PATENT AND TRADEMARK OFFICE
CERTIFICATE OF CORRECTION

PATENT NO. : 4,581,389

DATED : April 8, 1986

INVENTOR(S) : Roland SCHAEFER

It is certified that error appears in the above-identified patent and that said Letters Patent is hereby corrected as shown below:

COLUMN 8 (Claim 20), line 59, delete "polymerizable"

(second instance).

COLUMN 8 (Claim 21), line 65, delete "polymerizable"

(second instance).

Signed and Sealed this
Ninth Day of December, 1986

Attest:

DONALD J. QUIGG

*Attesting Officer*  *Commissioner of Patents and Trademarks*